United States Patent
Zhang et al.

(10) Patent No.: US 12,017,931 B2
(45) Date of Patent: Jun. 25, 2024

(54) STATIC WATER STERILIZATION MODULE

(71) Applicant: NINGBO SUNPU LED CO., LTD., Zhejiang (CN)

(72) Inventors: Yaohua Zhang, Zhejiang (CN); Yuanbao Du, Zhejiang (CN); Zhongjie Lin, Zhejiang (CN); Mingda Xu, Zhejiang (CN); Yingguo Yang, Zhejiang (CN); Fusheng Chen, Zhejiang (CN); Xiaoqing Zhu, Zhejiang (CN); Qinghao Zhang, Zhejiang (CN)

(73) Assignee: NINGBO SUNPU LED CO., LTD., Zhejiang (CN)

( * ) Notice: Subject to any disclaimer, the term of this patent is extended or adjusted under 35 U.S.C. 154(b) by 407 days.

(21) Appl. No.: 17/552,385

(22) Filed: Dec. 16, 2021

(65) Prior Publication Data
US 2022/0194818 A1    Jun. 23, 2022

(30) Foreign Application Priority Data

Dec. 17, 2020 (CN) .......................... 202023055665.2

(51) Int. Cl.
    *C02F 1/32*     (2023.01)
    *A61L 2/10*     (2006.01)
    *A61L 2/26*     (2006.01)

(52) U.S. Cl.
    CPC .............. *C02F 1/325* (2013.01); *A61L 2/10* (2013.01); *A61L 2/26* (2013.01); *A61L 2202/11* (2013.01);
    (Continued)

(58) Field of Classification Search
    CPC ............... C02F 1/325; C02F 2201/004; C02F 2201/3222; C02F 2201/3228;
    (Continued)

(56) References Cited

U.S. PATENT DOCUMENTS

2009/0200215 A1* 8/2009 Bathula .................. C02F 1/008
                                                         210/260
2023/0165985 A1    6/2023 Jeong et al.

FOREIGN PATENT DOCUMENTS

CN      111068088 A    4/2020
KR    20200089174 A    7/2020

OTHER PUBLICATIONS

The the Korean 1st Office Action issued on Nov. 27, 2023 for KR10-2021-0175622.

* cited by examiner

*Primary Examiner* — Nicole M Ippolito
*Assistant Examiner* — Hanway Chang
(74) *Attorney, Agent, or Firm* — Yue (Robert) Xu; Apex Attorneys at Law, LLP

(57) ABSTRACT

A static water sterilization module is provided according to the present application, which includes a lamp holder, a light-transmitting plate, a lamp plate, a sterilization lamp, a first sealing ring, a clamping member and a waterproof potting adhesive. The light-transmitting plate is mounted on the lamp holder. The lamp plate is mounted in the lamp holder. The sterilization lamp is mounted on the lamp plate. An inner surface of the lamp plate, an inner surface of the light-transmitting plate and an inner wall of the lamp holder form a sealing chamber for mounting the sterilization lamp. The first sealing ring abuts against an outer surface of the lamp plate. The clamping member is configured to press the first sealing ring and the lamp plate. The waterproof potting adhesive is configured to encapsulate a base chamber between the outer surface of the lamp plate and the lamp holder.

10 Claims, 3 Drawing Sheets

(52) U.S. Cl.
CPC ... *A61L 2202/121* (2013.01); *C02F 2201/004* (2013.01); *C02F 2201/3222* (2013.01); *C02F 2201/3228* (2013.01); *C02F 2303/04* (2013.01)

(58) Field of Classification Search
CPC .......... C02F 2303/04; A61L 2/10; A61L 2/26; A61L 2202/11; A61L 2202/121
See application file for complete search history.

STATIC WATER STERILIZATION MODULE

The present application claims the priority to Chinese Patent Application No. 202023055665.2, titled "STATIC WATER STERILIZATION MODULE", filed on Dec. 17, 2020 with the China National Intellectual Property Administration, which is incorporated herein by reference in its entirety.

FIELD

The present application relates to the technical field of water purification, and in particular to a static water sterilization module.

BACKGROUND

A sterilization lamp is generally adopted in a conventional static water sterilization module for sterilization.

However, the conventional static water sterilization module has no waterproof treatment on a back surface of a lamp body, that is, a wire and a back of a lamp plate are exposed to the air, so that the water vapor may enter the static water sterilization module from the wire and the lamp plate, which results in fog vapor on a light-transmitting surface, and weakens the sterilization effect of the static water sterilization module.

Therefore, how to improve the sterilization effect of the static water sterilization module is an urgent technical problem to be solved by those skilled in the art.

SUMMARY

An object according to the present application is to provide a static water sterilization module, and the sterilization effect of the static water sterilization module is improved.

In order to achieve the above object, a static water sterilization module is provided according to the present application, which includes:
 a lamp holder;
 a light-transmitting plate, where the light-transmitting plate is mounted on the lamp holder;
 a lamp plate, where the lamp plate is mounted in the lamp holder;
 a sterilization lamp, where the sterilization lamp is mounted on the lamp plate, and an inner surface of the lamp plate, an inner surface of the light-transmitting plate and an inner wall of the lamp holder form a sealing chamber for mounting the sterilization lamp;
 a first sealing ring, where the first sealing ring abuts against an outer surface of the lamp plate;
 a clamping member configured to press the first sealing ring and the lamp plate; and
 a waterproof potting adhesive configured to encapsulate a base chamber between the outer surface of the lamp plate and the lamp holder.

Preferably, the static water sterilization module further includes a second sealing ring abutting against an outer surface of the light-transmitting plate, a limiting portion for accommodating the second sealing ring is provided at an end of the lamp holder away from the light-transmitting plate, and the second sealing ring abuts against the limiting portion.

Preferably, the second sealing ring and/or the first sealing ring are colored sealing rings.

Preferably, the waterproof potting adhesive is wrapped outside of the clamping member and outside of the first sealing ring.

Preferably, the static water sterilization module further includes a reflective cup mounted on the lamp plate, the reflective cup is sleeved on an outer side of the sterilization lamp, and the reflective cup is located in the sealing chamber.

Preferably, the reflective cup has a metal structure or a polytetrafluoroethylene structure.

Preferably, the static water sterilization module further includes a threaded locking member, the threaded locking member is a threaded locking cover, a through hole for a wire to pass through is defined on a cover body of the threaded locking member, the through hole is in clearance fit with the wire, a side wall of the threaded locking member is threadly connected to an outer wall of the lamp holder, and the waterproof potting adhesive is located in an inner chamber of the threaded locking member.

Preferably, the clamping member is an annular buckle cock spirally clamped to an inner wall of the lamp holder.

Preferably, the number of spirals on the lamp holder threadly connected to the clamping member is not more than one turn.

Preferably, the lamp plate is a heat-dissipating lamp plate, and the waterproof potting adhesive is a thermal conductive adhesive.

In the above technical solution, the static water sterilization module provided according to the present application includes the lamp holder, the light-transmitting plate, the lamp plate, the sterilization lamp, the first sealing ring, the clamping member and the waterproof potting adhesive. The light-transmitting plate is mounted on the lamp holder. The lamp plate is mounted in the lamp holder. The sterilization lamp is mounted on the lamp plate. The inner surface of the lamp plate, the inner surface of the light-transmitting plate and the inner wall of the lamp holder form the sealing chamber for mounting the sterilization lamp. The first sealing ring abuts against the outer surface of the lamp plate. The clamping member is configured to press the first sealing ring and the lamp plate. The waterproof potting adhesive is configured to encapsulate the base chamber between the outer surface of the lamp plate and the lamp holder.

As can be seen from the above description, in the static water sterilization module provided according to the present application, a back of the sterilization lamp is sealed by the first sealing ring and the clamping member, and the back chamber of the sterilization lamp is sealed as a whole by the waterproof potting adhesive, so as to prevent liquid and water vapor from entering the static water sterilization module. In the sterilization lamp provided according to the present application, the light is effectively used, and the sterilization effect of the static water sterilization module is improved.

BRIEF DESCRIPTION OF THE DRAWINGS

For more clearly illustrating embodiments of the present application or the technical solutions in the conventional technology, drawings referred to for describing the embodiments or the conventional technology will be briefly described hereinafter. Apparently, the drawings in the following description are only examples of the present application, and for the person skilled in the art, other drawings may be obtained based on the drawings provided without any creative efforts.

Figure 1:
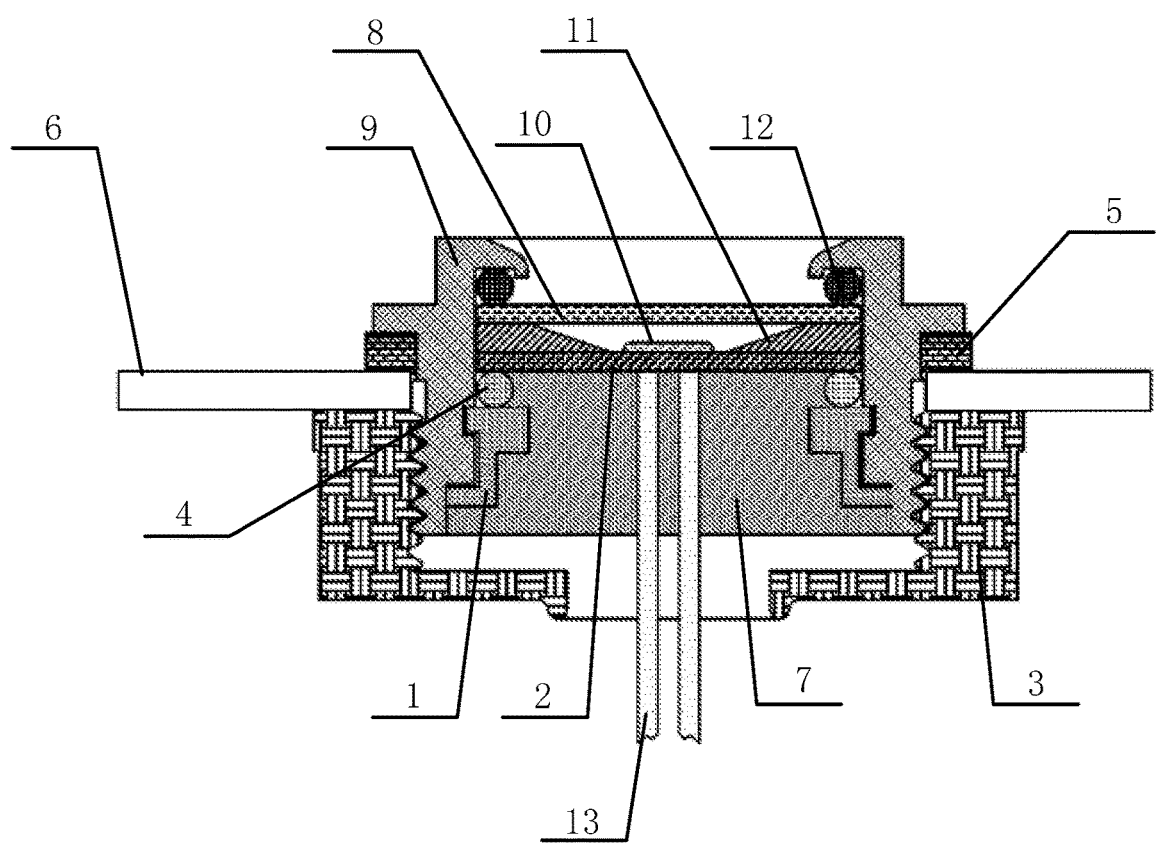
FIG. 1 is a sectional view of a static water sterilization module provided according to an embodiment of the present application.
Figure 2:
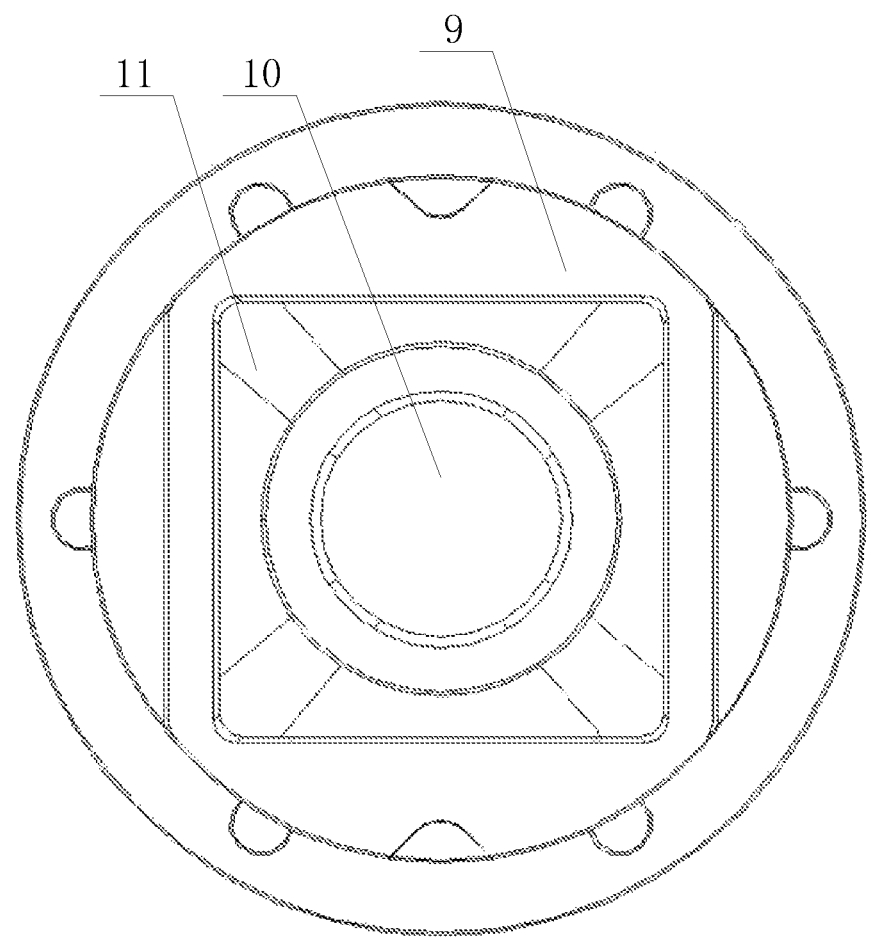
FIG. 2 is a top view of the static water sterilization module provided according to the embodiment of the present application.
Figure 3:
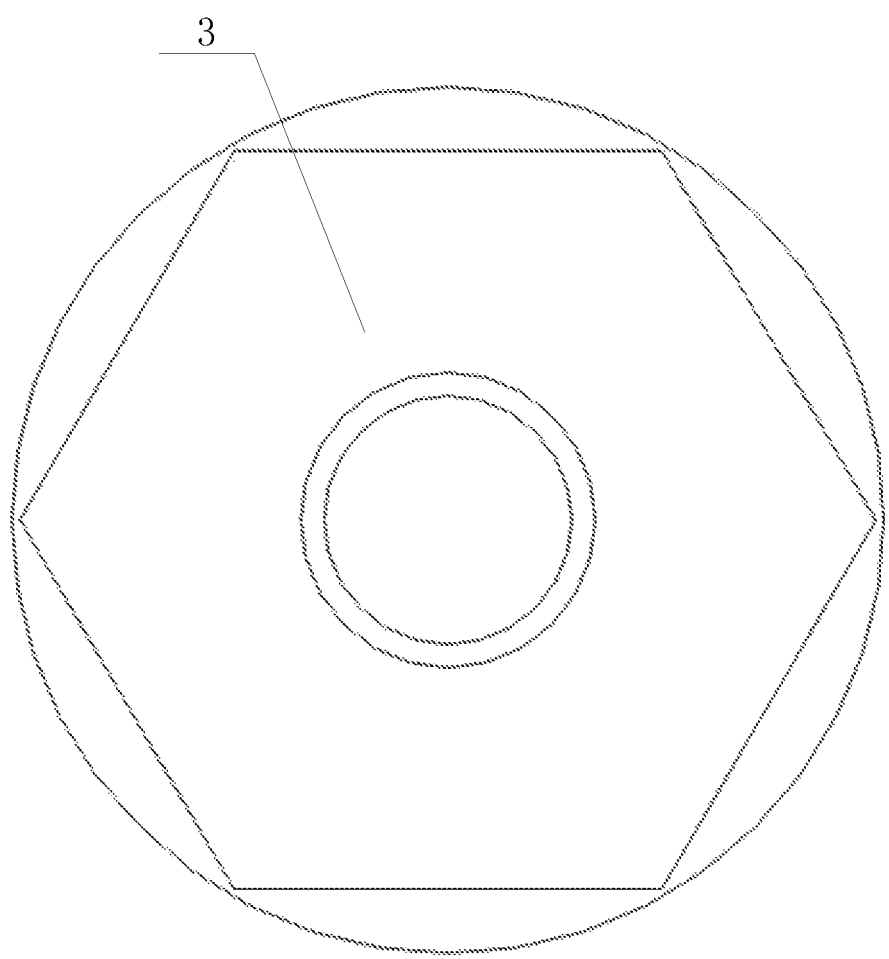
FIG. 3 is a bottom view of the static water sterilization module provided according to the embodiment of the present application.

Reference numerals in FIGS. 1 to 3 are as follows:

| | |
|---|---|
| 1 clamping member, | 2 lamp plate; |
| 3 threaded locking member, | 4 first sealing ring, |
| 5 outer waterproof sealing ring, | 6 water tank bottom plate, |
| 7 waterproof potting adhesive, | 8 light-transmitting plate, |
| 9 lamp holder, | 10 sterilization lamp, |
| 11 reflective cup, | 12 second sealing ring, |
| 13 wire. | |

DETAILED DESCRIPTION OF THE EMBODIMENTS

A core of the present application is to provide a static water sterilization module, and the sterilization effect of the static water sterilization module is improved.

In order to make those skilled in the art better understand technical solutions of the present application, the present application will be described in detail hereinafter in conjunction with the drawings and specific embodiments.

Referring to FIGS. 1 to 3.

In a specific embodiment, a static water sterilization module provided according to the present application includes a lamp holder 9, a light-transmitting plate 8, a lamp plate 2, a sterilization lamp 10, a first sealing ring 4, a clamping member 1 and a waterproof potting adhesive 7.

The light-transmitting plate 8 is mounted on the lamp holder 9. Preferably, the light-transmitting plate 8 is a glass plate, and may specifically be a quartz glass sheet. Since the quartz glass sheet has the weakest transmitting ability in the UVC band, the quartz glass sheet is the best among all UV-transmitting materials, which improves the sterilization effect of the static water sterilization module.

The lamp plate 2 is mounted in the lamp holder 9. Specifically, the lamp holder 9 is sleeved on an outer side of the lamp plate 2, and an inner wall of the lamp holder 9 may abut against an outer wall of the lamp plate 2.

The sterilization lamp 10 is mounted on the lamp plate 2, and an inner surface of the lamp plate 2, an inner surface of the light-transmitting plate 8 and an inner wall of the lamp holder 9 form a sealing chamber for mounting the sterilization lamp 10. Preferably, the sterilization lamp 10 may be a lamp bead. Specifically, a UVLED ultraviolet sterilization light source may be used, and the lamp bead may be directly welded to the lamp plate 2. Preferably, the lamp plate 2 has a heat dissipation function, which prolongs the service life of the static water sterilization module. During wiring, a wire 13 is arranged on a back surface of the lamp plate 2 for supplying power to the sterilization lamp 10.

The first sealing ring 4 abuts against an outer surface of the lamp plate 2. The clamping member 1 is configured to press the first sealing ring 4 and the lamp plate 2. The waterproof potting adhesive 7 is configured to encapsulate a base chamber between the outer surface of the lamp plate 2 and the lamp holder 9. Specifically, the waterproof potting adhesive 7 fills a back chamber of the lamp holder 9.

Preferably, the sterilization lamp 10 is arranged close to the light-transmitting plate 8. The closer the sterilization lamp 10 is to an irradiated object, the larger an irradiation range of the sterilization lamp 10 is, and the larger the irradiation range of the sterilization lamp 10 is, the better the effect is.

The waterproof potting adhesive 7 fully fills the back surface of the lamp plate 2, and immerses a space from an outer side of the clamping member 1 to the inner wall of the lamp holder 9. In order to improve the sealing performance of the sterilization lamp 10, the outer side of the clamping member 1 is wrapped with the waterproof potting adhesive 7, and an outer side of the first sealing ring 4 is wrapped with the waterproof potting adhesive 7, so as to further prevent the water vapor from entering the static water sterilization module from the back of the lamp plate 2.

In order to improve the heat dissipation effect, preferably, the waterproof potting adhesive 7 is a thermal conductive adhesive.

The sterilization lamp 10 is arranged upward, so as to prevent the water vapor from entering the sterilization lamp 10 from the lamp plate 2 at bottom.

It can be known from the above description that in the static water sterilization module provided according to the specific embodiment of the present application, a back of the sterilization lamp 10 is sealed by the first sealing ring 4 and the clamping member 1, and the back chamber of the sterilization lamp 10 is sealed as a whole by the waterproof potting adhesive 7, which prevents the liquid and water vapor from entering the static water sterilization module. In the present application, the light of the sterilization lamp 10 is effectively used, and the sterilization effect of the static water sterilization module is improved.

As shown in FIG. 1, in order to improve sealing performance, preferably, the static water sterilization module further includes a second sealing ring 12 abutting against an outer surface of the light-transmitting plate 8, a limiting portion for accommodating the second sealing ring 12 is provided at an end of the lamp holder 9 away from the light-transmitting plate 8, and the second sealing ring 12 abuts against the limiting portion. Specifically, the limiting portion is arranged in an annular shape, and after the static water sterilization module is assembled, the second sealing ring 12 closely abuts against the limiting portion and the light-transmitting plate 8.

In a specific embodiment, the second sealing ring 12 and/or the first sealing ring 4 are colored sealing rings, which may specifically be red, blue or black sealing rings. Preferably, the colors of the first sealing ring 4 and the second sealing ring 12 are different from the color of the lamp holder 9. More specifically, the second sealing ring 12 and the first sealing ring 4 are sealing rings of different colors. In case of assembling, it is confirmed whether the first sealing ring 4 and the second sealing ring 12 are missing during assembly, so as to prevent the product from losing its due waterproof effect.

In a specific embodiment, the static water sterilization module further includes the lamp plate 2 mounted on the lamp holder 9 and a reflective cup 11 mounted on the lamp plate 2, the reflective cup 11 is sleeved on an outer side of the sterilization lamp 10, and the reflective cup 11 is located in the sealing chamber. Specifically, the reflective cup 11 has a conical ring structure, and is flared in a direction of the light-transmitting plate 8. Specifically, a reflective surface of the reflective cup 11 may be formed by multiple successively connected planes.

Specifically, the reflective cup 11 is of a metal structure or a polytetrafluoroethylene (PTFE) structure. Specifically, the reflective cup 11 may be made of aluminum. In a case that the reflective cup is made of PTFE, because the UVC light is not harmful to the PTFE and the PTFE material has a high reflectivity to the UVC band, thus achieving a good light concentration. In this way, the originally wasted light is used, the sterilization effect is improved, and the lamp holder 9 is prevented from aging when irradiated by the light.

In a specific embodiment, the static water sterilization module further includes a threaded locking member 3, which may specifically be a nut. As shown in FIG. 1, preferably, the threaded locking member 3 is a threaded locking cover, a through hole for the wire 13 to pass through is defined on a cover body of the threaded locking member 3, a side wall of the threaded locking member 3 is threadly connected to an outer wall of the lamp holder 9. Preferably, the through hole is in clearance fit with the wire 13. The waterproof potting adhesive 7 is located in an inner chamber of the threaded locking member 3. In the present application, the threaded locking member 3 is designed in a shape of a bottom cap with a hole defined in the middle to lead out the wire 13, so that an internal structure of the product cannot be seen from the outside, which protects the waterproof potting adhesive 7 from being damaged and protects sundries from entering the product. In addition, the threaded locking cover is similar to a cover body and wraps the back of the static water sterilization module, so that the static water sterilization module is more beautiful, simple to operate and convenient to assemble.

In a case that the static water sterilization module is connected to the outside, an end of the threaded locking member 3 abuts against the external structure, and the lamp holder 9 may abut against and is lock with an external component through an outer waterproof sealing ring 5, that is, a clamping groove for mounting the static water sterilization module is formed between the lamp holder 9 and the end of the threaded locking member 3. As shown in FIG. 1, a water tank bottom plate 6 is located between the threaded locking member 3 and the outer waterproof sealing ring 5. The threaded locking member 3 is tightened, and the outer waterproof sealing ring 5 abuts against the water tank bottom plate 6 to prevent water from entering from the outside.

On the basis of the above solutions, preferably, the clamping member 1 is an annular buckle cock threadly clamped to the inner wall of the lamp holder 9. In a case that the clamping member 1 is locked with the lamp holder 9, the clamping member 1 abuts against a spiral groove on the lamp holder 9.

In order to improve assembly efficiency, preferably, the number of spirals of the spiral grooves on the lamp holder 9 threadly connected to the clamping member 1 is not more than one turn. Specifically, the spiral groove on the lamp holder 9 is an inner recessed inclined groove body clamped with the clamping member 1. In the present application, the clamping member 1 is arranged as a buckle type, a first sealing ring 4 is added between the clamping member 1 and the lamp plate 2, and the clamping member 1 is screwed only once during assembly, so that internal components in the static water sterilization module fit better, the internal components is protected from being squeezed by the annular buckle cock, and waterproof is realized.

The above embodiments are described in a progressive manner. Each of the embodiments is mainly focused on describing its differences from other embodiments, and reference may be made among these embodiments with respect to the same or similar parts.

Based on the above description of the disclosed embodiments, those skilled in the art are capable of carrying out or using the present application. It is obvious for the person skilled in the art to make various modifications to these embodiments. The general principle defined herein may be applied to other embodiments without departing from the spirit or scope of the present application. Therefore, the present application is not limited to the embodiments described herein, but should be in accordance with the broadest scope consistent with the principle and novel features disclosed herein.

The invention claimed is:

1. A static water sterilization module, comprising:
   a lamp holder;
   a light-transmitting plate, wherein the light-transmitting plate is mounted on the lamp holder;
   a lamp plate, wherein the lamp plate is mounted in the lamp holder;
   a sterilization lamp, wherein the sterilization lamp is mounted on the lamp plate, and an inner surface of the lamp plate, an inner surface of the light-transmitting plate and an inner wall of the lamp holder form a sealing chamber for mounting the sterilization lamp;
   a first sealing ring, wherein the first sealing ring abuts against an outer surface of the lamp plate;
   a clamping member configured to press the first sealing ring and the lamp plate; and
   a waterproof potting adhesive configured to encapsulate a base chamber between the outer surface of the lamp plate and the lamp holder.

2. The static water sterilization module according to claim 1, further comprising a second sealing ring abutting against an outer surface of the light-transmitting plate, wherein a limiting portion for accommodating the second sealing ring is provided at an end of the lamp holder away from the light-transmitting plate, and the second sealing ring abuts against the limiting portion.

3. The static water sterilization module according to claim 2, wherein the second sealing ring and/or the first sealing ring are colored sealing rings.

4. The static water sterilization module according to claim 1, the waterproof potting adhesive is wrapped outside of the clamping member and outside of the first sealing ring.

5. The static water sterilization module according to claim 1, further comprising a reflective cup mounted on the lamp plate, wherein the reflective cup is sleeved on an outer side of the sterilization lamp, and the reflective cup is located in the sealing chamber.

6. The static water sterilization module according to claim 5, wherein the reflective cup is of a metal structure or a polytetrafluoroethylene structure.

7. The static water sterilization module according to claim 1, further comprising a threaded locking member, wherein the threaded locking member is a threaded locking cover, a through hole for a wire to pass through is defined on a cover body of the threaded locking member, the through hole is in clearance fit with the wire, a side wall of the threaded locking member is threadly connected to an outer wall of the lamp holder, and the waterproof potting adhesive is located in an inner chamber of the threaded locking member.

8. The static water sterilization module according to claim 1, wherein the clamping member is an annular buckle cock threadly connected to an inner wall of the lamp holder.

9. The static water sterilization module according to claim 8, wherein the number of spirals on the lamp holder threadly connected to the clamping member is not more than one turn.

10. The static water sterilization module according to claim 1, wherein the lamp plate is a heat-dissipating lamp plate, and the waterproof potting adhesive is a thermal conductive adhesive.

* * * * *